US012806007B2

(12) United States Patent
Nelson et al.

(10) Patent No.: US 12,806,007 B2
(45) Date of Patent: Nov. 24, 2026

(54) DEVICES, SYSTEMS, AND METHODS FOR CONTROLLING DEPLOYMENT OF A MEDICAL DEVICE

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: Mitchell Nelson, Hudson, WI (US); Troy Anthony Giese, Blaine, MN (US); Joel T. Eggert, Plymouth, MN (US); Jason John Matteson, Jr., Beldenville, WI (US); Christopher J. Koudela, New London, MN (US); Dana Sachs, Pine City, MN (US)

(73) Assignees: BOSTON SCIENTIFIC SCIMED, INC., Maple Grove, MN (US); MAYO FOUNDATION FOR MEDICAL EDUCATION AND RESEARCH, Minnesota (MN)

( * ) Notice: Subject to any disclaimer, the term of this patent is extended or adjusted under 35 U.S.C. 154(b) by 761 days.

(21) Appl. No.: 18/140,591

(22) Filed: Apr. 27, 2023

(65) Prior Publication Data

US 2023/0346543 A1 Nov. 2, 2023

Related U.S. Application Data

(60) Provisional application No. 63/335,995, filed on Apr. 28, 2022.

(51) Int. Cl.

| | |
|---|---|
| ***A61F 2/24*** | (2006.01) |
| ***A61B 17/122*** | (2006.01) |
| *A61B 17/04* | (2006.01) |

(52) U.S. Cl.

CPC .............. *A61F 2/24* (2013.01); *A61F 2/2427* (2013.01); *A61F 2/2457* (2013.01);

(Continued)

(58) Field of Classification Search

CPC .... A61F 2/2427; A61F 2/2439; A61F 2/2466; A61F 2/2457; A61B 2017/0488;

(Continued)

(56) References Cited

U.S. PATENT DOCUMENTS

| | | | |
|---|---|---|---|
| 5,667,513 | A | 9/1997 | Torrie et al. |
| 5,702,397 | A | 12/1997 | Goble et al. |

(Continued)

FOREIGN PATENT DOCUMENTS

| | | | |
|---|---|---|---|
| EP | 3104772 | B1 | 3/2019 |
| GB | 2579420 | A | 6/2020 |

(Continued)

OTHER PUBLICATIONS

International Search Report and Written Opinion for the International Application No. PCT/US2020/040678, mailed Oct. 16, 2020, 10 pages.

(Continued)

*Primary Examiner* — Dinah Baria

(74) *Attorney, Agent, or Firm* — SEAGER, TUFTE & WICKHEM, LLP

(57) ABSTRACT

A delivery/deployment system for delivering an implantable device within an implantable device housing and for deploying the implantable device from the implantable device housing. A stylet may be used to longitudinally advance or retract the implantable device with respect to the implantable device housing, such as to extend and deploy the implantable device from the implantable device housing. The delivery/deployment system has an implantable-device-extension-limiter arrangement configured to limit the dis- (Continued)

tance which the implantable device may be extended from the implantable device housing. The delivery/deployment system optionally also has an implantable-device-rotation-limiter arrangement configured to limit rotation of the implantable device with respect to the implantable device housing.

8 Claims, 10 Drawing Sheets

(52) U.S. Cl.
CPC .... *A61F 2/2466* (2013.01); *A61B 2017/0409* (2013.01); *A61B 2017/0488* (2013.01); *A61B 2017/0496* (2013.01); *A61F 2220/0016* (2013.01)

(58) Field of Classification Search
CPC .... A61B 2017/0464; A61B 2017/0409; A61B 17/128; A61B 17/0401
See application file for complete search history.

(56) References Cited

U.S. PATENT DOCUMENTS

| | | | | |
|---|---|---|---|---|
| 7,736,388 | B2 | 6/2010 | Goldfarb et al. | |
| 8,252,050 | B2 | 8/2012 | Maisano et al. | |
| 8,303,622 | B2 | 11/2012 | Alkhatib | |
| 8,852,088 | B2 | 10/2014 | Ransden et al. | |
| 9,572,667 | B2 | 2/2017 | Solem | |
| 9,681,864 | B1 | 6/2017 | Gammie et al. | |
| 10,136,993 | B1 | 11/2018 | Metchik et al. | |
| 10,179,236 | B2 | 1/2019 | Haasl et al. | |
| 10,478,629 | B2 | 11/2019 | An et al. | |
| 10,945,718 | B2 | 3/2021 | Hiorth et al. | |
| 2004/0088003 | A1 | 5/2004 | Leung et al. | |
| 2004/0230280 | A1 | 11/2004 | Cates et al. | |
| 2006/0207607 | A1 | 9/2006 | Hirotsuka et al. | |
| 2006/0276890 | A1 | 12/2006 | Solem et al. | |
| 2007/0080188 | A1 | 4/2007 | Spence et al. | |
| 2007/0118151 | A1 | 5/2007 | Davidson | |
| 2008/0051863 | A1 | 2/2008 | Schneider et al. | |
| 2008/0195126 | A1 | 8/2008 | Solem | |
| 2009/0105729 | A1 | 4/2009 | Zentgraf | |
| 2011/0060407 | A1 | 3/2011 | Ketai et al. | |
| 2011/0301699 | A1 | 12/2011 | Saadat | |
| 2012/0130492 | A1 | 5/2012 | Eggli et al. | |
| 2012/0172892 | A1 | 7/2012 | Grubac et al. | |
| 2013/0096611 | A1 | 4/2013 | Sullivan | |
| 2013/0110230 | A1 | 5/2013 | Solem | |
| 2014/0046347 | A1 | 2/2014 | Cully | |
| 2015/0250590 | A1 | 9/2015 | Gries et al. | |
| 2017/0245993 | A1 | 8/2017 | Gross et al. | |
| 2017/0252032 | A1 | 9/2017 | Hiorth et al. | |
| 2018/0185153 | A1 | 7/2018 | Bishop et al. | |
| 2018/0250133 | A1 | 9/2018 | Reich et al. | |
| 2018/0296327 | A1 | 10/2018 | Dixon et al. | |
| 2018/0303614 | A1 | 10/2018 | Schaffner et al. | |
| 2019/0059876 | A1 * | 2/2019 | Decker | A61B 17/0401 |
| 2019/0314634 | A1 | 10/2019 | Deininger et al. | |
| 2019/0343634 | A1 | 11/2019 | Garvin et al. | |
| 2020/0163768 | A1 | 5/2020 | Apkarian et al. | |
| 2020/0261699 | A1 | 8/2020 | Rizq et al. | |
| 2021/0000597 | A1 | 1/2021 | Shuey et al. | |
| 2021/0000598 | A1 | 1/2021 | Shuey et al. | |
| 2021/0000599 | A1 | 1/2021 | Shuey et al. | |
| 2021/0007847 | A1 | 1/2021 | Eggert et al. | |
| 2022/0015904 | A1 | 1/2022 | Hiorth et al. | |
| 2022/0022863 | A1 | 1/2022 | Hiorth et al. | |
| 2022/0096235 | A1 | 3/2022 | Giese et al. | |
| 2023/0062599 | A1 | 3/2023 | Walker et al. | |
| 2023/0123832 | A1 | 4/2023 | Abbott et al. | |

FOREIGN PATENT DOCUMENTS

| | | | |
|---|---|---|---|
| GB | 2579433 | A | 6/2020 |
| WO | 2006039199 | A2 | 4/2006 |
| WO | 2006039199 | A3 | 5/2006 |
| WO | 2008014191 | A2 | 1/2008 |
| WO | 2008014191 | A3 | 10/2008 |
| WO | 2012014201 | A2 | 2/2012 |
| WO | 2012014201 | A3 | 4/2012 |
| WO | 2015193728 | A2 | 12/2015 |
| WO | 2020109596 | A1 | 6/2020 |
| WO | 2020123719 | A1 | 6/2020 |
| WO | 2020219281 | A1 | 10/2020 |
| WO | 2021035050 | A1 | 2/2021 |
| WO | 2021076820 | A1 | 4/2021 |
| WO | 2021080782 | A1 | 4/2021 |
| WO | 2021086903 | A1 | 5/2021 |
| WO | 2022106497 | A1 | 5/2022 |

OTHER PUBLICATIONS

International Search Report and Written Opinion for the International Patent Application No. PCT/US2020/040672, mailed Oct. 16, 2020.

"Fish Fighter® Kwik-Pull™ Anchor Retriever" Fish Fighter Products, 6 pages, URL: https://fishfighterproducts.com/shop/fish-fighter-kwik-pull-anchor-retriever/ Retrieved Aug. 29, 2020.

"Knotless SutureTak® Anchor" Arthrex, 2 pages, 1 page, URL: https://www.arthrex.com/resources/animation/2d7_OmxWw0edpgFLMMbz5A/knotless-suturetak-anchor. Retrieved Aug. 29, 2020.

"Shoulder Labral Repair with Knotless Suture Tak® Anchor" Arthrex, retrieved Aug. 29, 2020, URL: https://www.arthrex.com/resources/animation/9cpCPTZLCEGvYQFMdIKwxg/shoulder-labral-repair-with-knotless-suturetak-anchor 7 pages. Retrieved Aug. 29, 2020.

"Knotless SutureTak Anchor Instability Repair" Arthrex, 6 pages, 2018.

APS—Annapolis Performance Sailing., "Ronstan Constrictor Rope Clutch| Expert Review"—YouTube, 3 pages. Retrieved Oct. 9, 2020.

International Search Report and Written Opinion for the International Patent Application No. PCT/US2021/051722, mailed Jan. 7, 2022, 10 pages.

International Search Report and Written Opinion for the International Patent Application No. PCT/US2022/042085, mailed Dec. 5, 2022, 11 pages.

Invitation to Pay Additional Fees and, where applicable Protest Fees, for International Application No. PCT/US2022/042098, date of mailing, Dec. 2, 2022, 13 pages.

International Search Report and Written Opinion dated Jul. 10, 2023 for International Application No. PCT/US2023/020285.

* cited by examiner

DEVICES, SYSTEMS, AND METHODS FOR CONTROLLING DEPLOYMENT OF A MEDICAL DEVICE

CROSS-REFERENCE TO RELATED APPLICATIONS

This application claims the benefit of priority of U.S. Provisional Application No. 63/335,995, filed Apr. 28, 2022, the entire disclosure of which is hereby incorporated by reference herein for all purposes.

FIELD

The present disclosure relates generally to the field of implantable medical devices. More particularly, the present disclosure relates to devices, systems, and methods for controlling deployment of a medical device such as an implantable medical device. Even more particularly, the present disclosure relates to devices, systems, and methods for controlling the depth of insertion of an implantable device into tissue and/or rotation of an implantable device with respect to the tissue.

BACKGROUND

Various transluminal techniques (e.g., transcatheter techniques) provide minimally invasive solutions to treat or to repair a site within the body without requiring open, more invasive surgery. However, it may be difficult to control the deployment of the implantable device. The transluminal deployment of an implantable device typically requires a delivery/deployment system assembly of one or more catheters, shafts, coils, rods, etc., to maneuver through tortuous paths within the body and to deliver an implantable device and system to the treatment site. Moreover, an implantable device and system typically are pushed distally from the delivery/deployment system to anchor the device into tissue at the treatment site. There typically is minimal room in such delivery/deployment system for additional components, and visualization may be challenging.

It is generally desirable to deploy an implantable device to a desired depth within the tissue, without extending too far and potentially inadvertently perforating or puncturing through the implant tissue wall. Therefore, it generally is desirable to deploy the implantable device from its associated delivery/deployment system to a prescribed distance with every implant, regardless of the position of the delivery/deployment system, to verify that the implantable device has been successfully deployed. However, the delivery/deployment system typically undergoes varying levels of stress, steerability, and compression to deliver the implantable device and associated system, potentially adversely impacting predictability of the distance the implantable device moves with respect to the delivery/deployment system. Accordingly, there is a need for improvements to devices, systems, and methods for delivering and deploying an implantable device, such as by controlling the depth of insertion of an implantable device (e.g., so as not to puncture the tissue into which the implantable device is inserted).

Additionally or alternatively, it is often desirable to withdraw a delivery/deployment system from an implantable device without causing such withdrawal to impact the site (e.g., tissue) in which the implantable device has been implanted. Typically, the delivery/deployment system moves in one or more directions (i.e., axially and/or rotationally) with respect to the implantable device being delivered/deployed. It is desirable for such movement of the delivery/deployment system not to cause movement of the implantable device with respect to the implant site, which may put undue stress on body tissue at the implant site (e.g., to resist the movement of the implantable device). Accordingly, there is a need for improvements to devices, systems, and methods for delivering and deploying a tissue anchor, such as by controlling movement of the tissue anchor during deployment and implantation (e.g., to release from the deployment device and system without affecting the tissue in which the tissue anchor is implanted).

Various improvements to translumenal repair devices, systems, and methods would be welcome. Furthermore, solutions with applicability to other surgical fields as well would be of interest and value as well.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, an anchor garage is configured to limit the extent a tissue anchor housed therein travels distally out of said anchor garage. In some aspects, the anchor garage has a wall defining a lumen configured to house a tissue anchor therein, and a stopper extending radially inwardly from said anchor garage wall into the lumen and positioned to limit distal travel of an elongate member operatively coupled to a tissue anchor within the anchor garage to extend the tissue anchor distally out of the anchor garage.

In some embodiments, the stopper has a tab formed by a cut in the anchor garage wall and bent radially-inwardly into the lumen defined within the anchor garage.

In some embodiments, the stopper is configured to fit within a longitudinal groove in an anchor housing of an anchor positioned within the anchor garage lumen to limit rotational movement of the anchor with respect to the anchor garage.

In some embodiments, a longitudinal slot is defined in the anchor garage wall sized to receive a rotational stopper projecting radially-outwardly from an anchor positioned within the anchor garage lumen to limit rotational movement of the anchor with respect to the anchor garage. In some embodiments, the longitudinal slot is positioned and configured to allow passage of a component therethrough for coupling with an anchor positioned within the anchor garage lumen.

In accordance with various principles of the present disclosure, a delivery/deployment system, for delivering and/or deploying a tissue anchor with respect to a treatment site, has a leaflet clip spreader; a leaflet clip operatively associated with the leaflet clip spreader; an anchor garage; an anchor operatively associated with the anchor garage; a stylet operatively coupled with the anchor to move the anchor distally with respect to the anchor garage; and an implantable-device-extension-limiter arrangement comprising an anchor garage stopper component operatively associated with the anchor garage; and a stylet stopper component operatively associated with the stylet. In some aspects, the stylet stopper component is configured to engage with the anchor garage stopper component to limit the distance the stylet may extend the anchor distally out of the anchor garage.

In some embodiments, the anchor garage has a wall defining a lumen therein, and the anchor is positionable within the anchor garage lumen. In some embodiments, the anchor garage stopper component comprises a tab formed by a cut in the anchor garage wall and bent radially-inwardly into the lumen defined within the anchor garage. In some embodiments, the stylet stopper component is a radially-expanded portion engageable with the tab in the anchor garage wall to limit distal extension thereof relative to the anchor garage. In some embodiments, the anchor has an anchor housing with a longitudinal groove into which the tab in the anchor garage wall extends to limit rotational movement of the anchor with respect to the anchor garage.

In some embodiments, the stylet is rotatably dissociable from the anchor; and the anchor includes a rotation-limiter component operatively engaged with an anchor garage rotation-limiter component to inhibit rotation of the anchor as the stylet is rotated. In some embodiments, the anchor garage has a wall defining a lumen therein; the anchor garage rotation-limiter component has a longitudinally extending slot in the anchor garage wall; the anchor is positioned within the anchor garage lumen; and the anchor rotation-limiter component includes a radially-outwardly extending projection extending into the slot in the anchor garage wall. In some embodiments, the anchor garage has a wall defining a lumen therein; the anchor is positioned within the anchor garage lumen; the anchor garage stopper component has a radially-inwardly extending component projecting into the anchor garage lumen; the anchor includes an anchor housing operatively associated therewith; the anchor rotation-limiter component has a longitudinally-extending groove extending along the anchor housing; and the anchor garage stopper component extends into the longitudinally-extending groove along the anchor housing to form the anchor garage rotation-limiter component. In some embodiments, the anchor garage stopper has a tab formed by a cut in the anchor garage wall and bent radially-inwardly into the lumen defined within the anchor garage and extending into the longitudinally-extending groove along the anchor housing.

In some embodiments, the anchor further includes a housing; an artificial chordae tendineae tensioning and locking device is operatively associated with the anchor housing; the system further includes an artificial chordae tendineae coupled between the leaflet clip and the artificial chordae tendineae tensioning and locking device; the stylet is operatively coupled with the artificial chordae tendineae tensioning and locking device to actuate the artificial chordae tendineae tensioning and locking device; and the anchor has a rotation-limiter component operatively engaged with an anchor garage rotation-limiter component to inhibit rotation of the anchor as the stylet is rotated to actuate the artificial chordae tendineae tensioning and locking device. In some embodiments, the anchor garage has a wall defining a lumen therein; the anchor garage rotation-limiter component includes a longitudinally extending slot in the anchor garage wall; the anchor is positioned within the anchor garage lumen; the anchor rotation-limiter component has a radially-outwardly extending projection extending into the slot in the anchor garage wall; and the artificial chordae tendineae extends from the leaflet clip to the anchor through the slot in the anchor garage wall.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers followed by a prime ('), and redundant description is generally omitted for the sake of brevity. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
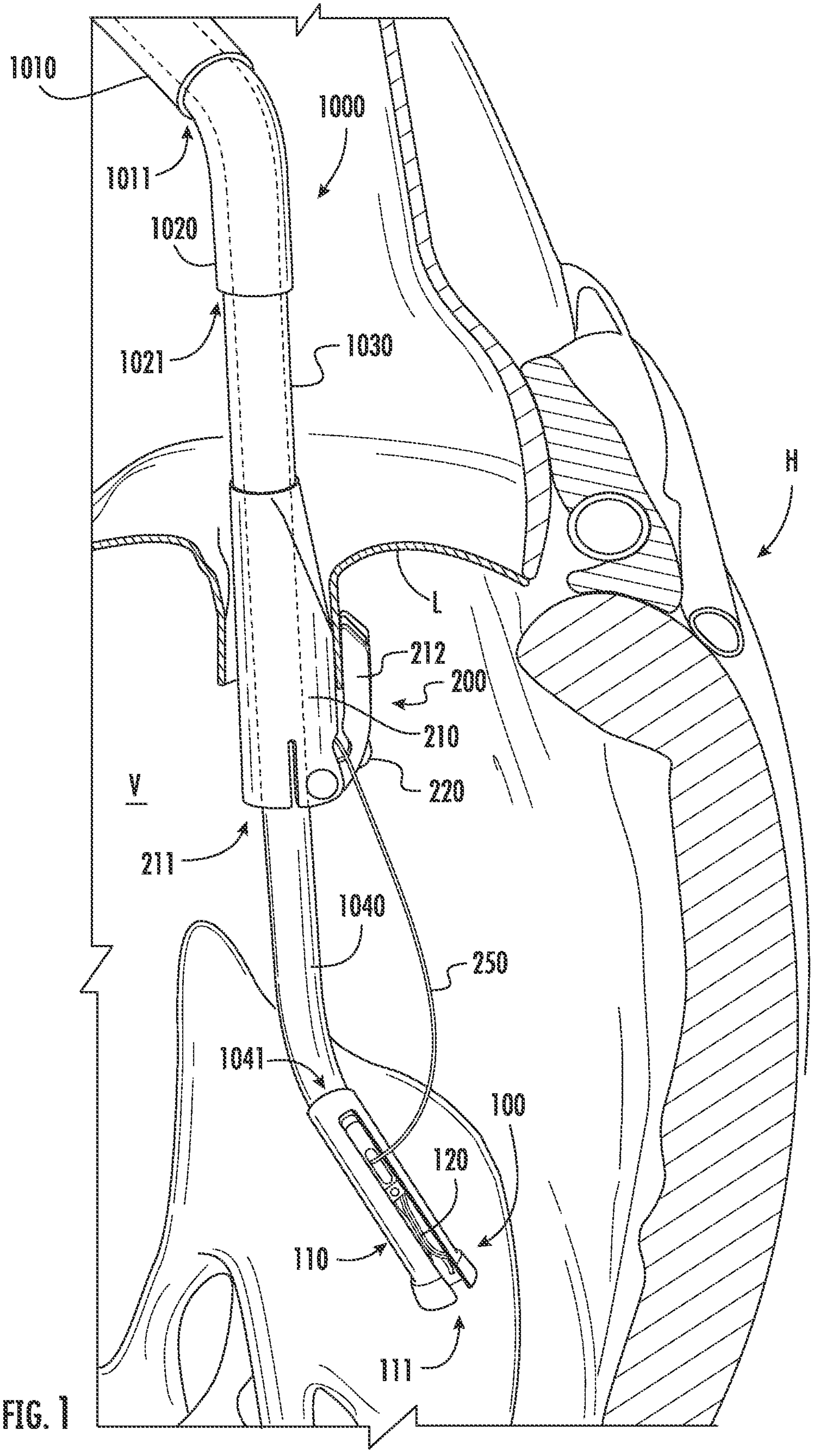
FIG. 1 illustrates a perspective view of an example of an embodiment of a delivery/deployment device and system formed in accordance with various principles of the present disclosure shown in a schematic representation of a heart.

The following detailed description should be read with reference to the drawings, which depict illustrative embodiments. It is to be understood that the disclosure is not limited to the particular embodiments described, as such may vary.

All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, “proximal” refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and/or closest to a delivery device, and “distal” refers to the direction or location furthest from the user, such as when using the device (e.g., introducing the device into a patient, or during implantation, positioning, or delivery), and/or closest to a delivery device. “Longitudinal” means extending along the longer or larger dimension of an element. A “longitudinal axis” extends along the longitudinal extent of an element, though is not necessarily straight and does not necessarily maintain a fixed configuration if the element flexes or bends. “Central” means at least generally bisecting a center point and/or generally equidistant from a periphery or boundary, and a “central axis” means, with respect to an opening, a line that at least generally bisects a center point of the opening, extending longitudinally along the length of the opening when the opening comprises, for example, a tubular element, a strut, a channel, a cavity, or a bore. As used herein, a “channel” or “bore” is not limited to a circular cross-section. As used herein, a “free end” of an element is a terminal end at which such element does not extend beyond. Finally, it will be appreciated that terms such as portion, area, section, segment, etc., may be used interchangeably herein without intent to limit, reference generally being made to a section as a general region, and a segment as a particular part, for the sake of convenient differentiation and without intent to limit.

Heart disease, including atrioventricular heart valve malfunctions, impedes patient cardiac output, which reduces patient quality of life and lifespan. The proper flow of blood through the heart is regulated, inter alia, by heart valves, including atrioventricular heart valves, which include soft tissue leaflets which cyclically open and close to allow blood to flow through in one direction. Healthy leaflets prevent blood flow in the opposite direction (regurgitation). Chordae tendineae, extending from the leaflets to the papillary muscles, support the proper functioning of the leaflets, such as by distributing load to the papillary muscles during systolic closure, and by preventing the leaflet from flailing into the atrium. Improper functioning of the chordae tendineae compromises the capacity of the leaflets to form a seal at the heart valve. Various defects of failure of the chordae tendineae, such as elongation, rupture, thickening, retraction, calcification, inelastic stretching or other changes in elasticity, etc., may result in improper closure of the heart valve and/or a flailing leaflet that may no longer have the capacity to form a valving seal for normal heart function. The compromised ability of the leaflets to form a seal typically results in valve regurgitation, or backflow of blood, which typically prevents an adequate supply of blood to be delivered through the cardiovascular system.

Heart valve disease is typically repaired via invasive surgical intervention (e.g., open surgery, involving cutting open the patient), or by complicated pinching of the leaflets together creating dual, smaller openings, or a replacement of the native valve. These approaches involve opening into the patient’s chest and heart chamber to expose the heart valve for direct viewing and repair. Resection, partial removal, and/or repair of the patient’s leaflets along with the implantation of a surgical ring are complex techniques used by surgeons to reduce the diameter of the patient’s heart valve annulus, thus allowing the leaflets to properly coapt and reduce regurgitate flow. Some techniques may slightly reduce regurgitate flow but may not provide a durable solution and do not repair and/or replace damaged chordae tendineae of a valve. Various transluminal techniques (e.g., transcatheter techniques) provide minimally invasive solutions to repair a heart valve, such as the leaflets thereof. Transcatheter artificial valve replacement is less invasive than open surgery techniques, though typically are followed by lifelong treatment with anticoagulants. Transcatheter edge-to-edge fixation of the leaflets is another minimally invasive option, though typically prevents the option for future minimally invasive valve replacement. Various improvements to such systems and devices and methods would be welcome.

In accordance with various principles of the present disclosure, a delivery/deployment system is configured to provide repeatable and predictable delivery and/or deployment of an implantable device, such as repeatable and predictable depth of insertion of such implantable device into an implant site. It will be appreciated that reference may be made herein to an anatomical site, delivery site, deployment site, implant/implantation site, target site, treatment site, etc., interchangeably and without intent to limit. It will further be appreciated that terms such as implant (and other grammatical forms thereof) may be used interchangeably herein with terms (and grammatical forms thereof) such as affix, anchor, attach, associate, couple, engage, embed, hold, retain, purchase, secure, etc., without intent to limit. In some embodiments, the extent to which an implantable device is extended from a delivery/deployment system (and, generally, into the treatment site as well) is determined by the geometry and configuration of the delivery and deployment devices rather than by control of various elongate members delivering the implantable device, and thus is not affected by any potential compression of the delivery/deployment system. In some aspects, the delivery and deployment devices are not as susceptible to compression as the various elongate members used therewith. For instance, the various elongate members typically are flexible, whereas the delivery and deployment devices tend to be not as flexible, and, in some instance, have thicker walls than the walls of flexible tubular elongate member used therewith and which may be susceptible to compression.

In accordance with various further principles of the present disclosure, a delivery/deployment system is configured to limit rotational movement of an implantable device during deployment thereof. For instance, the configuration and/or geometry of the implantable device and/or a device which delivers the implantable device inhibits rotation of the implantable device with respect to the treatment site when the implantable device is deployed (e.g., implanted into a treatment site), and/or when released from the delivery/deployment system. In some embodiments, the implantable device is delivered to the treatment site with or within a device such as a housing or garage. The housing or garage may be configured to interact with (e.g., operatively engage or engage to operate) the implantable device to inhibit rotational movement of the implantable device with respect to the treatment site and/or the housing or garage during deployment of the implantable device. In some embodiments, rotational movement of the implantable device is inhibited with respect to the devices and systems used to deliver such implantable device.

In some embodiments, the implantable device, and/or the device and/or system for delivering/deploying such device is shaped and configured to predictably and repeatably prescribe the depth of deployment of the implantable device as well as the rotational movement of the implantable device 200 with respect to the delivery/deployment device and system.

Principles of the present disclosure may be applied to various transluminal, such as transcatheter, device, systems, and methods for repairing heart valve dysfunction. An example of a technique for repairing heart valve dysfunction clipping a leaflet clip to a heart valve leaflet, extending an artificial chordae tendineae from the leaflet clip to the tissue of the heart wall (e.g., the ventricle, such as to papillary muscles), and anchoring the artificial chordae tendineae to the heart tissue with a tissue anchor. More particularly, a delivery/deployment system transcatheterally delivers a leaflet grasping mechanism, carrying (e.g., housing) a leaflet clip, to a heart valve. The leaflet grasping mechanism includes a clip spreader capable of bending open a spring arm of the leaflet clip to catch the free edge of a heart valve leaflet between the arms of the leaflet clip. The clip spreader then releases the spring arm to close and secure the leaflet clip on the leaflet. The delivery/deployment system is then advanced from the heart valve to the heart wall to extend an artificial chordae tendineae from the leaflet clip to the heart wall (typically the ventricle wall). An anchor garage, carrying (e.g., housing) a tissue anchor is brought to the desired implant location (e.g., papillary muscle) for the tissue anchor. The anchor garage may be delivered to the treatment site within the leaflet clip spreader and distally extendable therefrom, such as upon reaching the treatment site. Typically, the tissue anchor is delivered in a delivery configuration, which may be a compact or compressed or otherwise contracted configuration allowing transcatheter delivery thereof. The tissue anchor is extended from the anchor garage to expand into and be anchored to tissue at the implant site. The tension of the artificial chordae tendineae may be adjusted, such as by pulling on a proximal end of the artificial chordae tendineae extending through the delivery/deployment system to a proximal control end (such as a control handle) thereof. The desired or medically prescribed or indicated tension in the artificial chordae tendineae generally is achieved when the desired leaflet repair is achieved, resulting in proper valve functioning. An artificial chordae tendineae tensioning and locking device may be used to set the tension in and/or length of the artificial chordae tendineae. The leaflet clip spreader may remain in place with the leaflet clip until the proper valve function has been achieved, and then may be removed with the delivery/deployment system, leaving the leaflet clip in place. The delivery/deployment system may be retracted and, optionally, may cut the artificial chordae tendineae (e.g., upon withdrawal therefrom) and/or deliver another leaflet clip and artificial chordae tendineae and anchor set.

It will be appreciated that the term anchor (and other grammatical forms thereof) is used for the sake of convenience and may be used interchangeably herein with terms (and other grammatical forms thereof) such as anchor component, anchor device, anchor element, anchor mechanism, anchoring component, anchoring device, anchoring element, anchoring mechanism, and the like, such terms being known in the art to represent structures configured to hold another object in place. It will be appreciated that reference is made herein to a tissue anchor as an example of an embodiment of an implantable device. However, such reference is for the sake of convenience and without intent to limit, and tissue anchors/implantable devices usable with principles of the present disclosure are to be understood as including other devices. Moreover, it will be appreciated that principles described above are equally applicable to other devices, systems, and methods, the present disclosure not being limited to implantable devices.

Various embodiments of devices, systems, and methods formed In accordance with various principles of the present disclosure will now be described with reference to examples illustrated in the accompanying drawings. Reference in this specification to “one embodiment,” “an embodiment,” “some embodiments”, “other embodiments”, etc., indicates that one or more particular features, structures, concepts, and/or characteristics in accordance with principles of the present disclosure may be included in connection with the embodiment. However, such references do not necessarily mean that all embodiments include the particular features, structures, concepts, and/or characteristics, or that an embodiment includes all features, structures, concepts, and/or characteristics. Some embodiments may include one or more such features, structures, concepts, and/or characteristics, in various combinations thereof. It should be understood that one or more of the features, structures, concepts, and/or characteristics described with reference to one embodiment can be combined with one or more of the features, structures, concepts, and/or characteristics of any of the other embodiments provided herein. That is, any of the features, structures, concepts, and/or characteristics described herein can be mixed and matched to create hybrid embodiments, and such hybrid embodiment are within the scope of the present disclosure. Moreover, references to “one embodiment,” “an embodiment,” “some embodiments”, “other embodiments”, etc. in various places in the specification are not necessarily all referring to the same embodiment, nor are separate or alternative embodiments necessarily mutually exclusive of other embodiments. It should further be understood that various features, structures, concepts, and/or characteristics of disclosed embodiments are independent of and separate from one another, and may be used or present individually or in various combinations with one another to create alternative embodiments which are considered part of the present disclosure. Therefore, the present disclosure is not limited to only the embodiments specifically described herein, as it would be too cumbersome to describe all of the numerous possible combinations and subcombinations of features, structures, concepts, and/or characteristics, and the examples of embodiments disclosed herein are not intended as limiting the broader aspects of the present disclosure. The following description is of illustrative examples of embodiments only, and is not intended as limiting the broader aspects of the present disclosure.

In the drawings, it will be appreciated that common features are identified by common reference elements and, for the sake of brevity and convenience, and without intent to limit, the descriptions of the common features are generally not repeated. For purposes of clarity, not all components having the same reference number are numbered. A group of similar elements may be indicated by a number and letter, and reference may be made generally to one or such elements or such elements as a group by the number alone (without including the letters associated with each similar element. Moreover, certain features in one embodiment may be used across different embodiments and are not necessarily individually labeled when appearing in different embodiments.

Turning now to the drawings, FIG. 1 illustrates an example of an embodiment of an implantable device delivery/deployment system 100 formed in accordance with various principles of the present disclosure is illustrated being delivered to a treatment site (in this example of an embodiment, a heart ventricle V) by an example of an embodiment of a delivery/deployment system 1000. The delivery/deployment system 1000 includes a plurality of flexible elongate members, such as a delivery sheath 1010 which navigates and delivers the system 1000 to the region of the treatment site. A steerable delivery catheter 1020 extends within and through the delivery sheath 1010, and out the distal end 1011 of the delivery sheath 1010. The steerable delivery catheter 1020 is steerable to position the implantable device delivery/deployment system 100 and optionally another device delivery/deployment system 200 for delivery and/or deployment of respective devices carried thereby. The device delivery/deployment system 200 may be delivered with a device catheter 1030 extending through the steerable catheter 1020 and out the distal end 1021 thereof. An implantable device delivery catheter 1040 may extend through the device catheter 1030 to deliver the implantable device delivery/deployment system 100.

In the example of an embodiment illustrated in FIG. 1, the device catheter 1030 delivers a device delivery/deployment system 200 which includes a delivery/deployment device 210, illustrated in FIG. 1 in the form of a leaflet clip spreader 210 configured to deliver a leaflet clip 220 to a heart leaflet L. The device catheter 1030 may be referenced herein as a grasper shaft 1030 for the sake of convenience and to differentiate from other catheters described herein. The leaflet clip 220 is illustrated in FIG. 1 as being clamped onto a leaflet L by the spreader arm 212 of the leaflet clip spreader 210, with the leaflet clip 220 being shown in further detail in FIG. 2.

In the example of an embodiment illustrated in FIG. 1, the implantable device delivery/deployment system 100 is delivered on the distal end 1041 of a generally-flexible tubular elongate implantable device delivery catheter 1040 extending through the grasper shaft 1030. The example of an embodiment of an implantable device delivery/deployment system 100 illustrated in FIG. 1 includes an implantable device delivery/deployment device in the form of an anchor garage 110. As shown in further detail in FIG. 2, the distal end 1041 of the implantable device delivery catheter 1040 (which may be referenced herein as an anchor garage catheter 1040 for the sake of convenience) may be coupled to the proximal end 113 of the anchor garage 110, in any manner known to those of ordinary skill in the art. It will be appreciated that terms such as couple (and other grammatical forms thereof) may be used interchangeably herein with terms such as engage, grasp, hold, clasp, clip, anchor, attach, affix, secure, etc. (and other grammatical forms thereof), without intent to limit. The anchor garage 110 may be delivered to the treatment site within and through the leaflet clip spreader 210 to deliver an implantable device. An example of an embodiment of an implantable device is illustrated in FIG. 1, FIG. 2, FIGS. 4A-4D, FIG. 5A, and FIG. 5B as a tissue anchor 120 with talons 122 configured to penetrate into and extend within tissue to be anchored to the tissue, as described in further detail below. The anchor garage catheter 1040 is extendable distally out of the distal end 211 of the leaflet clip spreader 210 to deliver the anchor garage 110 to a desired anatomical site for implanting the anchor 120 such as illustrated in FIG. 1.

Figure 2:
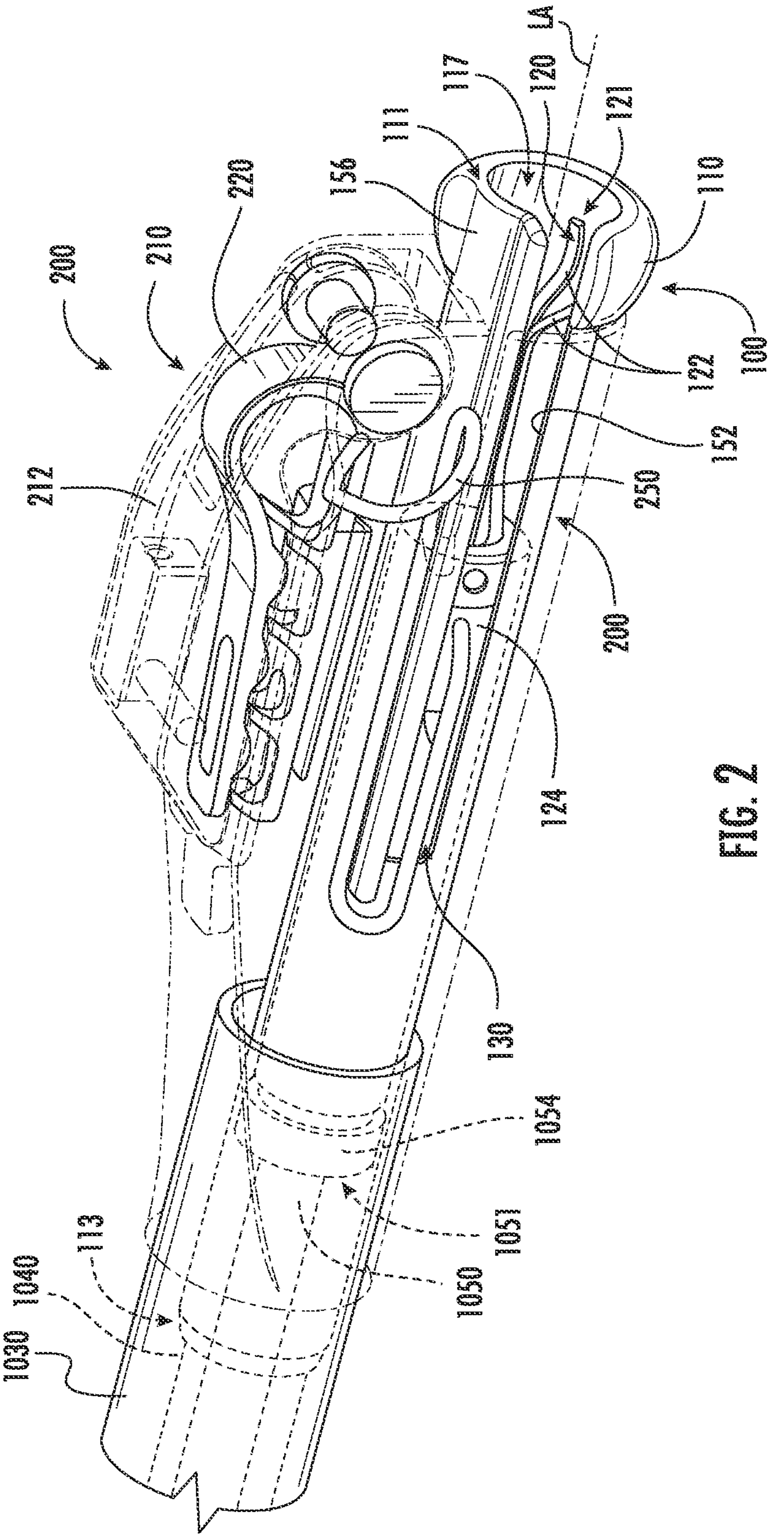
FIG. 2 illustrates a perspective view of an example of an embodiment of a delivery and deployment device and system formed in accordance with various principles of the present disclosure, with selected components thereof illustrated in phantom.

The anchor 120 may be delivered within a lumen 117 defined within the anchor garage 110. As illustrated in FIG. 2, the anchor 120 is delivered in a delivery configuration (e.g., a compact configuration) with the distal ends 121 of the talons 122 thereof within the anchor garage 110 and proximal to the distal end 111 of the anchor garage 110. The anchor 120 is extendable out of the distal end 111 of the anchor garage 110 to be implanted into tissue (e.g., into cardiac tissue such as papillary muscle tissue) in a deployed configuration (e.g., expanded, as illustrated in FIG. 4D and described in further detail below). The anchor garage 110 may have a blunt open distal end 111 (tip or free end) sized, shaped, configured, and dimensioned to facilitate pushing of the anchor garage 110 against cardiac tissue to deploy the anchor 120 out of the anchor garage 110 and into tissue at the deployment site without potentially pushing the distal end 111 of the anchor garage 110 into the cardiac tissue as well. Implantation of the anchor 120 into cardiac tissue secures an artificial chordae tendineae 250 (e.g., an expanded polytetrafluoroethylene (ePTFE) suture), extending from the leaflet clip 220 to the anchor 120, with respect to the heart wall (e.g., papillary muscle) to restore proper functioning of the leaflet L.

An artificial chordae tendineae tensioning and locking device 130 may be used to set the tension on the artificial chordae tendineae 250 as desired, indicated, necessary, etc. As illustrated in further detail in FIG. 5, the artificial chordae tendineae tensioning and locking device 130 may be coupled to the anchor 120. For instance, the artificial chordae tendineae tensioning and locking device 130 may be positioned within a housing 124 coupled to the anchor 120 (e.g., forming a part of the anchor 120 from which the talons 122 extend).

The anchor 120 of the implantable device delivery/deployment system 100 is delivered at the distal end 1051 of a stylet 1050, as illustrated in FIG. 2, FIGS. 4A-4D, FIG. 5A, and FIG. 5B. The stylet 1050 is operatively coupled with a proximal end 123 of the anchor 120 (e.g., threadedly coupled with, such as within, the proximal end 125 of the anchor housing 124) to advance or retract the anchor 120 with respect to the anchor garage 110 to deploy the anchor 120 such as by advancing the anchor 120 into tissue. For instance, the stylet 1050 may be axially advanced or retracted to axially advance or retract the anchor 120 with respect to the anchor garage 110. Additionally or alternatively, the stylet 1050 may be operatively coupled with the artificial chordae tendineae tensioning and locking device 130 to adjust tension applied by the artificial chordae tendineae tensioning and locking device 130 to the artificial chordae tendineae 250. For instance, in the example of an embodiment illustrated in FIG. 5A and FIG. 5B, a stylet coupler 1052 formed at the distal end 1051 of the stylet 1050 is operatively coupled with a tensioning coupler 134 operatively associated with the artificial chordae tendineae tensioning and locking device 130 such that movement of the stylet 1050 actuates the artificial chordae tendineae tensioning and locking device 130. In some embodiments, the stylet coupler 1052 and the tensioning coupler 134 are threadedly engaged within the proximal end 125 of the anchor housing 124, and are operatively coupled together such that rotation of the stylet 1050 imparts rotation to the tensioning coupler 134. As such, rotation of the stylet 1050 causes axial advancement or retraction of the tensioning coupler 134 to adjust the tension applied by the artificial chordae tendineae tensioning and locking device 130 to the artificial chordae tendineae 250. In the proximal-most position of the tensioning coupler 134, the artificial chordae tendineae tensioning and locking device 130 fixes or locks the tension on the artificial chordae tendineae 250. Further rotation of the stylet 1050 withdraws the stylet 1050 from the tensioning coupler 134 as well as from the anchor 120, such as to leave the anchor 120 deployed within the target tissue at the target site. It will be appreciated that other configurations of stylets, anchors, and artificial chordae tendineae tensioning and locking devices are within the scope and spirit of the present disclosure, the details of such elements not limiting the scope of the present disclosure.

Further details of structures and functions of a leaflet clip spreader, leaflet clip, anchor garage, anchor, artificial chordae tendineae, and artificial chordae tendineae tensioning and locking device, which do not limit the scope of the present disclosure, may be found, for example, in U.S. Patent Application Publication US2021/0007847, titled Devices, Systems, And Methods For Clamping A Leaflet Of A Heart Valve, and published on Jan. 14, 2021; U.S. Patent Application Publication US2021/0000597, titled Devices, Systems, And Methods For Adjustably Tensioning An Artificial Chordae Tendineae Between A Leaflet And A Papillary Muscle Or Heart Wall, and published on Jan. 7, 2021; U.S. Patent Application Publication US2021/0000599, titled Devices, Systems, And Methods For Artificial Chordae Tendineae, and published on Jan. 7, 2021; U.S. Patent Application Publication US2021/0000598, titled Devices, Systems, And Methods For Anchoring An Artificial Chordae Tendineae To A Papillary Muscle Or Heart Wall, and published on Jan. 7, 2021; U.S. Patent Application Publication No. 2022/0096235, titled Devices, Systems, And Methods For Adjustably Tensioning Artificial Chordae Tendineae In A Heart, and filed on Sep. 23, 2021; U.S. Patent Application Publication 2023/0123832, titled Devices, Systems, And Methods For Clamping A Leaflet Of A Heart Valve, and filed Sep. 1, 2021; U.S. Patent Application Publication 2023/0062599, titled Devices, Systems, And Methods For Anchoring An Artificial Chordae Tendineae To Cardiac Tissue, and filed Sep. 1, 2021; U.S. provisional patent application 63/279,473, titled Devices, Systems, And Methods For Positioning A Leaflet Clip, and filed Nov. 15, 2021; U.S. provisional patent application 63/291,758, titled Devices, Systems, And Methods For Positioning An Anchor For An Artificial Chordae Tendineae, and filed Dec. 20, 2021, all of which applications are hereby incorporated by reference herein in their entireties and for all purposes.

Figure 3:
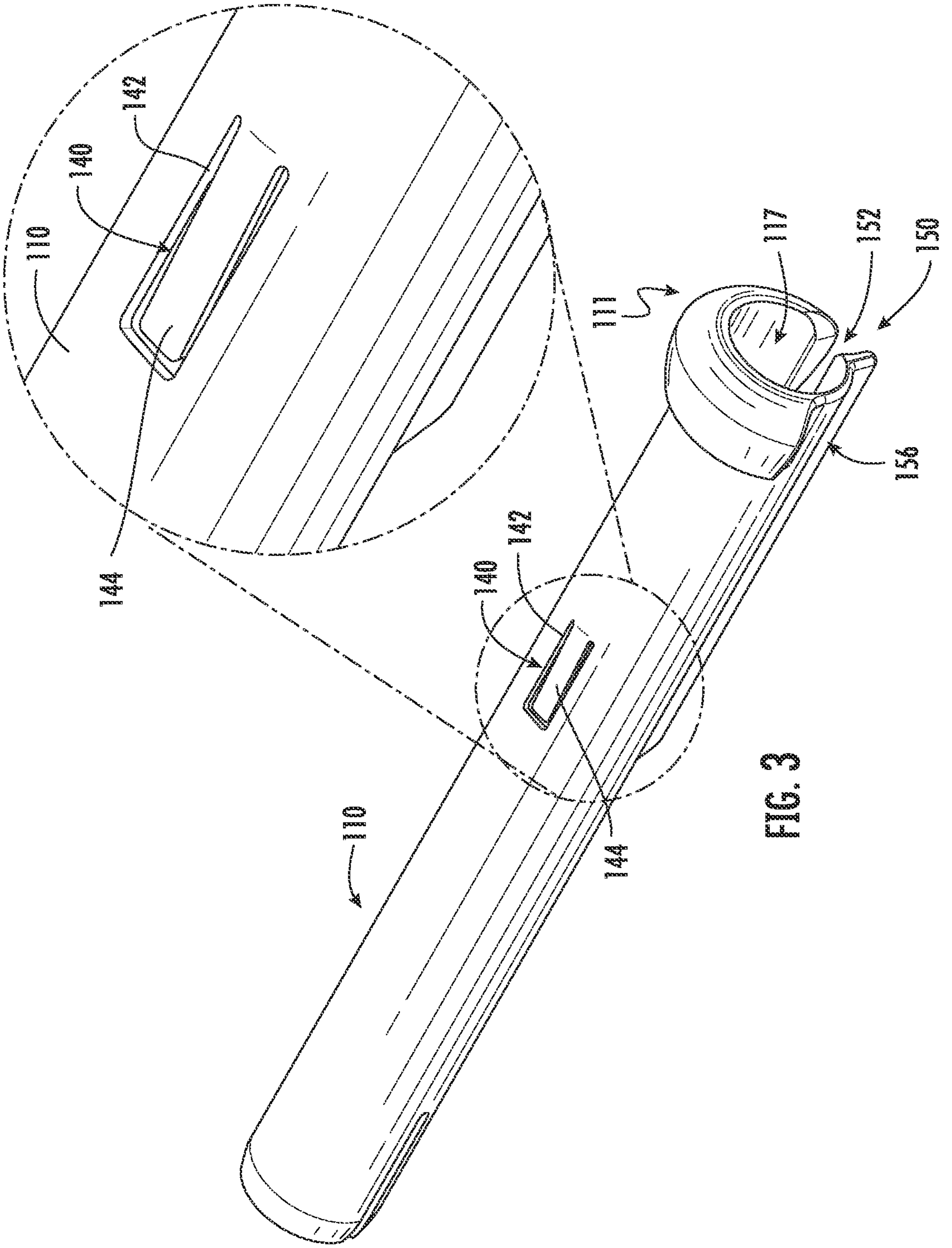
FIG. 3 is a perspective view of an example of an embodiment of an anchor delivery device formed in accordance with various principles of the present disclosure.

In accordance with various principles of the present disclosure, an implantable device delivery/deployment system 100 includes an implantable-device-extension-limiter arrangement shaped, positioned, and configured to limit the extension of an implantable device into tissue, such as to prevent inadvertent overextension with potentially adverse consequences. In some embodiments, the implantable-device-extension-limiter arrangement includes corresponding stopper components operatively associated with the anchor garage 110 and the stylet 1050 to limit distal extension of the stylet 1050 relative to the anchor garage 110 and thereby to limit distal extension of the anchor 120 to not exceed a desired extent, distance, etc., the anchor is advanced. For instance, the implantable-device-extension-limiter arrangement includes a stopper 140 associated with the anchor garage 110 and positioned to interact with a radially-expanded portion 1054 of the stylet 1050. In some embodiments, the anchor garage stopper 140 is a radially-inwardly extending component projecting into the lumen 117 defined within the anchor garage 110, such as illustrated in FIG. 5A and FIG. 5B. More particularly, in the example of an embodiment of an implantable device delivery/deployment system 100 illustrated in FIG. 3, FIG. 4A, FIG. 4B, FIG. 4C, FIG. 4D, FIG. 5A, and FIG. 5B, the stopper 140 is formed by a cut 142 in the wall of the anchor 120 forming a tab 144 which is pressed radially-inwardly into the lumen 117 within the anchor garage 110 (as illustrated in the detail view of FIG. 3). The cut 142 may be a laser cut, a machined cut, a sheared slot/groove, etc., or other suitable configuration known to those of ordinary skill in the art. The radially-expanded portion 1054 of the stylet 1050 in the example of an embodiment illustrated in FIG. 3, FIG. 4A, FIG. 4B, FIG. 4C, FIG. 4D, FIG. 5A, and FIG. 5B has a limited axial extent along the stylet 1050, with a larger radius than regions of the stylet 1050 proximal and distal thereto. The radially-expanded portion of the stylet 1050 may be referenced herein as a shoulder 1054 for the sake of convenience and without intent to limit.

It will be appreciated that formation of a stopper component as a radially-inwardly directed tab in the wall of the anchor garage 110 may facilitate assembly of the implantable device delivery/deployment system 100. In particular, the stopper 140 may act as a spring, allowing front loading of the anchor 120 into the anchor garage 110 (i.e., insertion from a distal to proximal direction along the anchor garage 110), and then returning to an implantable-device-extension-limiter configuration/position. Front loading of the implantable device delivery/deployment system 100 and delivery/deployment system 1000 in general may be desirable, such as to allow for an anchor garage 110 with an extended distal end 111 to be carried within a leaflet clip spreader 210 as depicted, for example, in FIG. 2.

Operation of the implantable-device-extension-limiter arrangement of the illustrated example of an embodiment of an implantable device delivery/deployment system 100 may be appreciated with reference to FIG. 4A, FIG. 4B, FIG. 4C, FIG. 4D, FIG. 5A, and FIG. 5B.

Figure 4A:
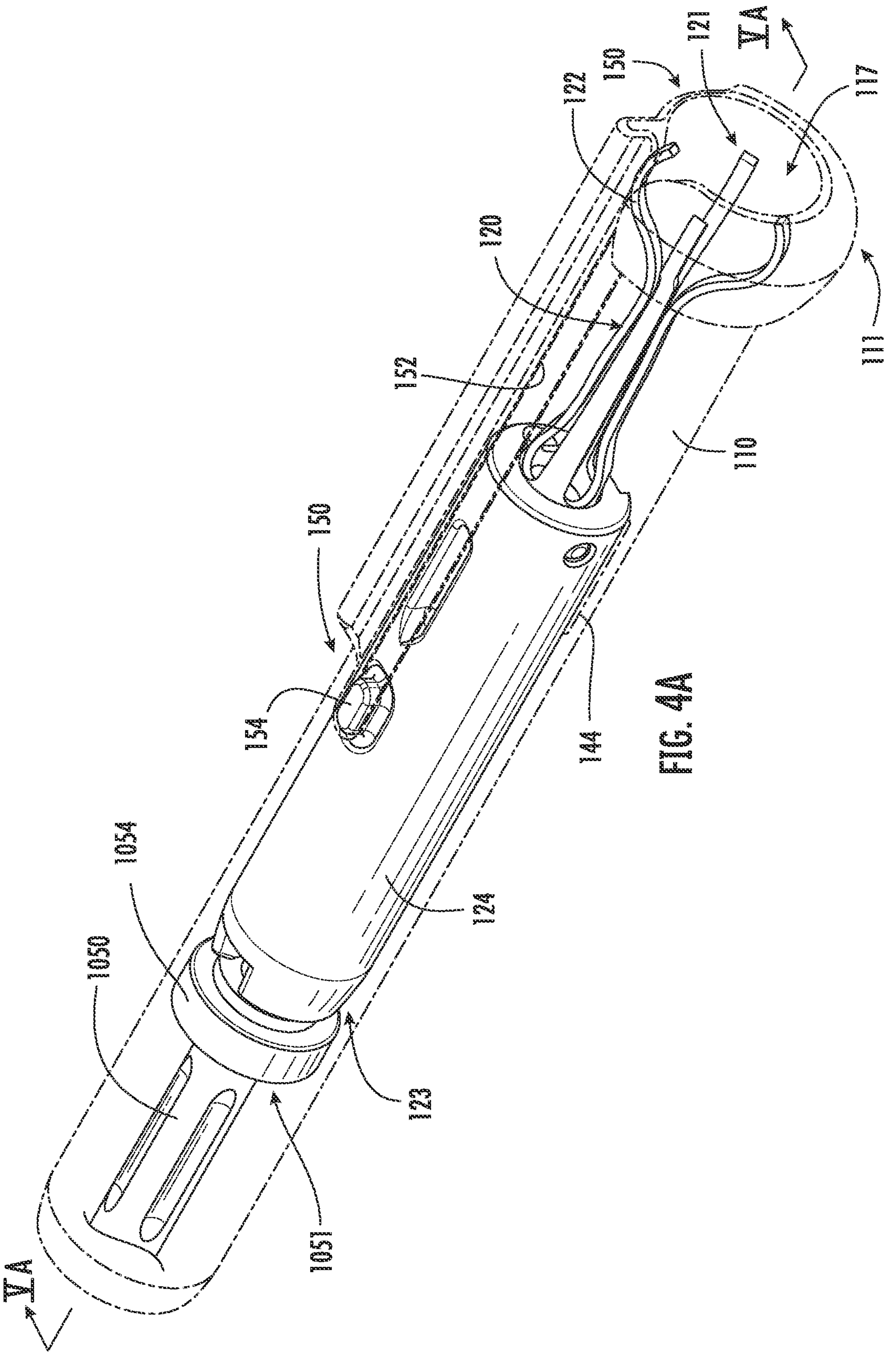
FIG. 4A illustrates a perspective view of an example of an embodiment of an anchor delivery and deployment device and system as in FIG. 2, with an anchor delivery device as in FIG. 3 illustrated in phantom, and showing an anchor housed therein in a delivery configuration.
Figure 5A:
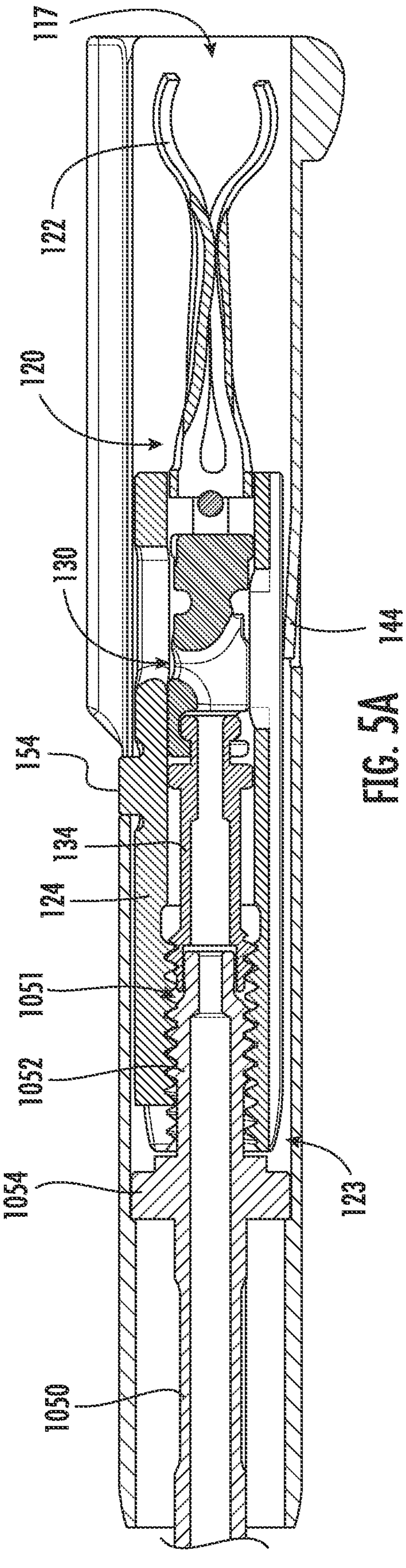
FIG. 5A illustrates a cross-sectional view along line VA-VA of FIG. 4A.
Figure 5B:
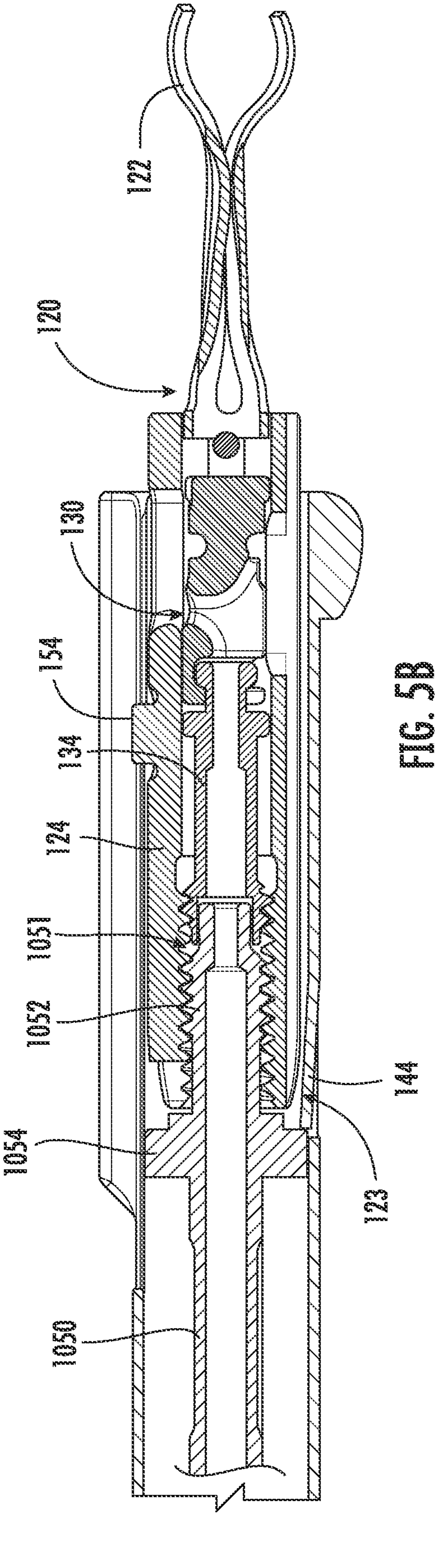
FIG. 5B illustrates a cross-sectional view along line VB-VB of FIG. 4D.

In FIG. 4A, the anchor 120 is illustrated in a delivery configuration within the anchor garage 110. The distal ends 121 of the talons 122 are proximal to the distal end 111 of the anchor garage 110. The shoulder 1054 of the stylet 1050 is proximally spaced apart from the tab 144 on the anchor garage 110, and thus capable of being moved distally with respect to the anchor garage 110. The relative positions of the shoulder 1054 and the tab 144 may be further appreciated with reference to the cross-sectional view along line VA-VA of FIG. 4A illustrated in FIG. 5A.

Figure 4B:
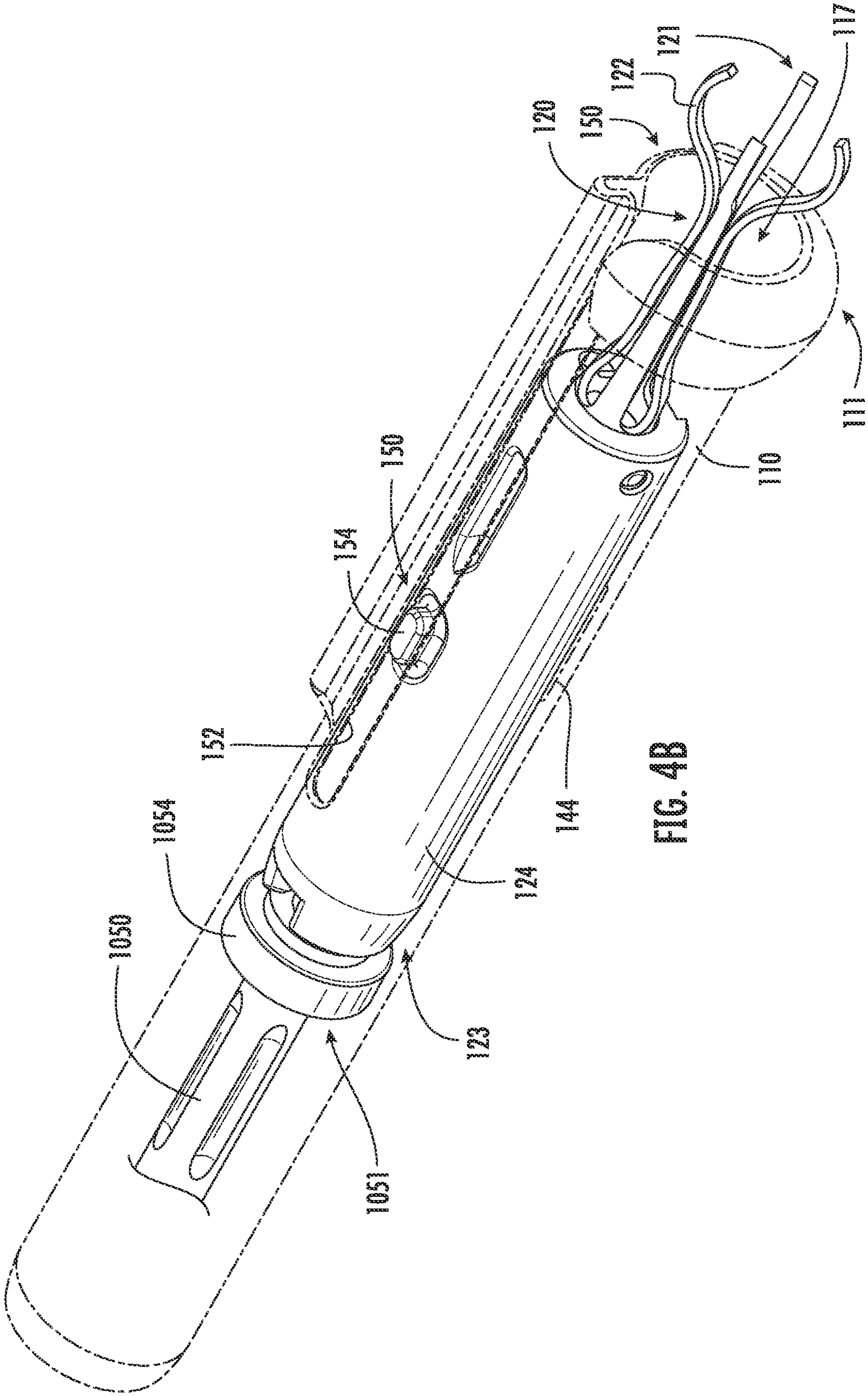
FIG. 4B illustrates a perspective view of an example of an embodiment of an anchor delivery and deployment device and system as in FIG. 4A, with the anchor beginning to be deployed.

As illustrated in FIG. 4B, distal advancement of the stylet 1050 causes the talons 122 of the anchor 120 to extend out from the distal end 111 of the anchor garage 110. In some embodiments, the distal ends 121 of the talons 122 are configured (e.g., tapered, pointed, etc.) to facilitate piercing or penetrating tissue. As noted above, in some embodiments, the distal end 111 of the anchor garage 110 may be blunt, so as not to damage tissue against which it is pressed. In use, the blunt distal end 111 of the anchor garage 110 may be pressed against tissue at the implantation site, and the stylet 1050 is distally advanced to cause the distal ends 121 of the talons 122 to extend out from the distal end 111 of the anchor garage 110 and to pierce into tissue at the implantation site.

Figure 4C:
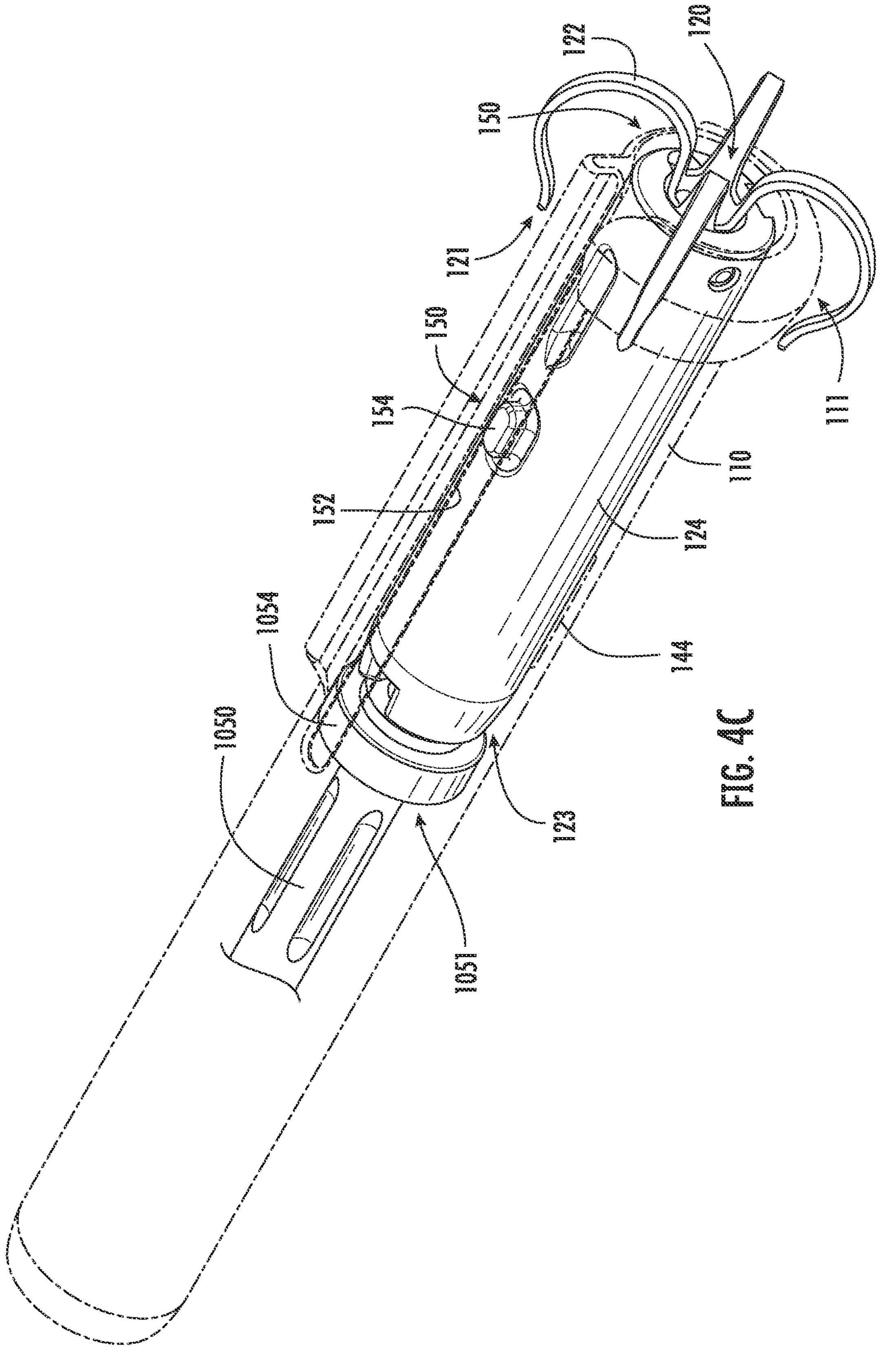
FIG. 4C illustrates a perspective view of an example of an embodiment of an anchor delivery and deployment device and system as in FIG. 4B, with the anchor in a partially deployed configuration.
Figure 4D:
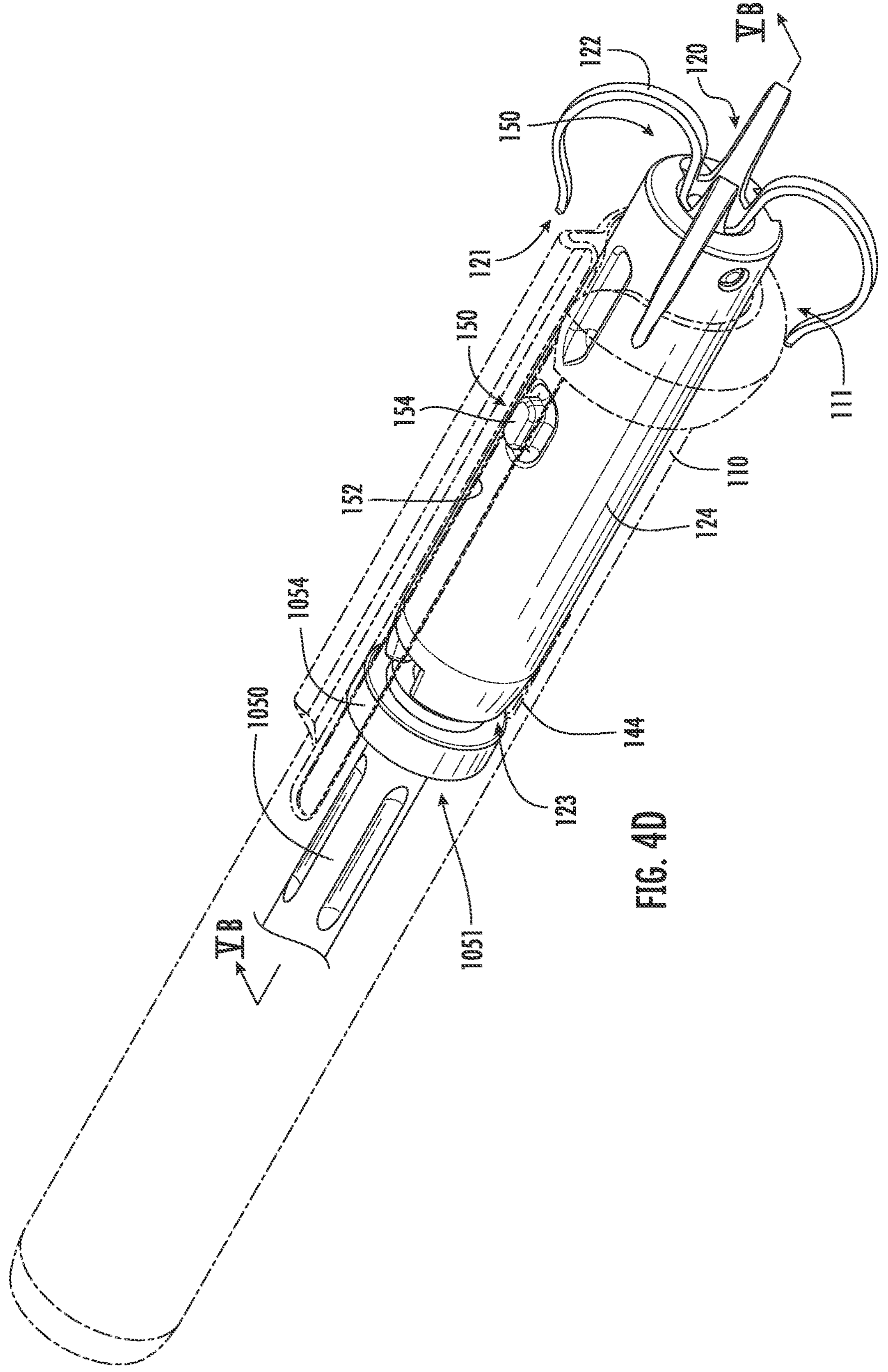
FIG. 4D illustrates a perspective view of an example of an embodiment of an anchor delivery and deployment device and system as in FIG. 4C, with the anchor in a deployed configuration.

Further distal advancement of the stylet 1050 causes the talons 122 of the anchor 120 to shift into a deployment configuration within tissue, as illustrated in FIG. 4C. The talons 122 may be formed of a superelastic or shape memory material such as nitinol (nickel-titanium alloy) so that once no longer within the anchor garage 110 (e.g., constrained or constricted or confined therein into a delivery configuration), the talons 122 substantially automatically (without further input or action thereon) shift to a deployment configuration. For instance, as illustrated in FIG. 4C, the example of an embodiment of an anchor 120 has talons 122 which curl, curve, bow, bend, etc., towards the proximal end 123 of the anchor 120.

The talons 122 reach their final deployment configuration when the distal end 131 of the anchor housing 124 reaches (and optionally extends out of) the distal end 111 of the anchor garage 110, as illustrated in FIG. 4D. As may be appreciated upon comparison of the relative positions of the stylet 1050 and the anchor garage 110 illustrated in FIGS. 4A-4D, the stylet 1050 is free to extend the anchor 120 distally out of the anchor garage 110 until the shoulder 1054 on the stylet 1050 is advanced into abutment with the stopper 140 (particularly, the tab 144) on the anchor garage 110, as illustrated in FIG. 4D, and in further detail in the cross-sectional view illustrated in FIG. 5B taken along line VB-VB in FIG. 4D. As such, the illustrated example of an embodiment of an implantable-device-extension-limiter arrangement predictably and repeatably limits the axially distal travel of the anchor 120 relative to the anchor garage 110 and relative to tissue, thereby predictably and repeatably managing the deployment extent, distance, depth, etc. (such terms and other such terms being used interchangeably herein without intent to limit) of the anchor 120 within tissue.

In accordance with various principles of the present disclosure, an implantable device delivery/deployment system 100 additionally or alternatively includes an implantable-device-rotation-limiter arrangement with rotation-limiter components shaped, positioned, and configured to limit rotational movement of an implantable device with respect to tissue in which the implantable device is implanted. In some embodiments, as described above, the stylet 1050 may be rotated to actuate the artificial chordae tendineae tensioning and locking device 130 and/or to be withdrawn/decoupled/dissociated (such terms and similar such terms, including other grammatical forms thereof, being used interchangeably herein without intent to limit) from the anchor 120. It may be desirable to limit rotation of the anchor 120 with the stylet 1050, such as to prevent unnecessary pressure or torque on the tissue in which the anchor 120 is implanted. In the example of an embodiment of an implantable device delivery/deployment system 100 illustrated in FIG. 3, FIG. 4A, FIG. 4B, FIG. 4C, FIG. 4D, FIG. 5A, and FIG. 5B, the implantable-device-rotation-limiter arrangement includes corresponding rotational-stopper elements 150 on the anchor garage 110 and the anchor housing 124 to limit rotational movement of the anchor housing 124 with respect to the anchor garage 110. For instance, in the illustrated example of an embodiment, the implantable-device-rotation-limiter arrangement includes a rotational stopper 154 (e.g., a projection or nub) associated with the anchor housing 124 (e.g., projecting radially-outwardly therefrom) and positioned within a longitudinally-extending slot 152 (i.e., extending generally parallel to the longitudinal axis LA of the device/system) defined within the anchor garage 110. The slot 152 allows longitudinal extension or retraction of the anchor 120 with respect to the anchor garage 110. However, the walls defining the slot 152 limit (e.g., prevent) rotational movement of the rotational stopper 154 within the slot 152, thereby limiting (e.g., preventing) rotational movement of the anchor 120 with respect to the anchor garage 110. As such, the stylet 1050 may be rotated with respect to the anchor 120 to actuate the artificial chordae tendineae tensioning and locking device 130 and/or to be withdrawn (e.g., separated, dissociated, etc.) from the anchor 120 to deploy the anchor 120 as described above without also rotating the anchor 120 within the tissue.

It will be appreciated with reference to FIG. 2 that the slot 152 may also facilitate coupling of the artificial chordae tendineae 250 between the leaflet clip 1050 and the anchor 120 by allowing the artificial chordae tendineae 250 to extend readily from the leaflet clip 220 into the lumen 117 of the anchor garage 110 (within which the anchor 120 is delivered) to be coupled with the anchor 120. The anchor garage 110 may also be formed with a leaflet clip spreader seat 156 with respect to which the leaflet clip spreader 210 may be seated, such as may be appreciated with reference to FIG. 2 and FIG. 3. It will be appreciated that the slot 152 is circumferentially spaced apart from the leaflet clip spreader seat 156, such as to allow the rotational stopper 154 on the anchor housing 124 to move within the slot 152 in the anchor garage 110 and/or to allow the artificial chordae tendineae 250 to extend from the leaflet clip 1050 to the anchor 120 within the anchor garage 110.

Figure 6:
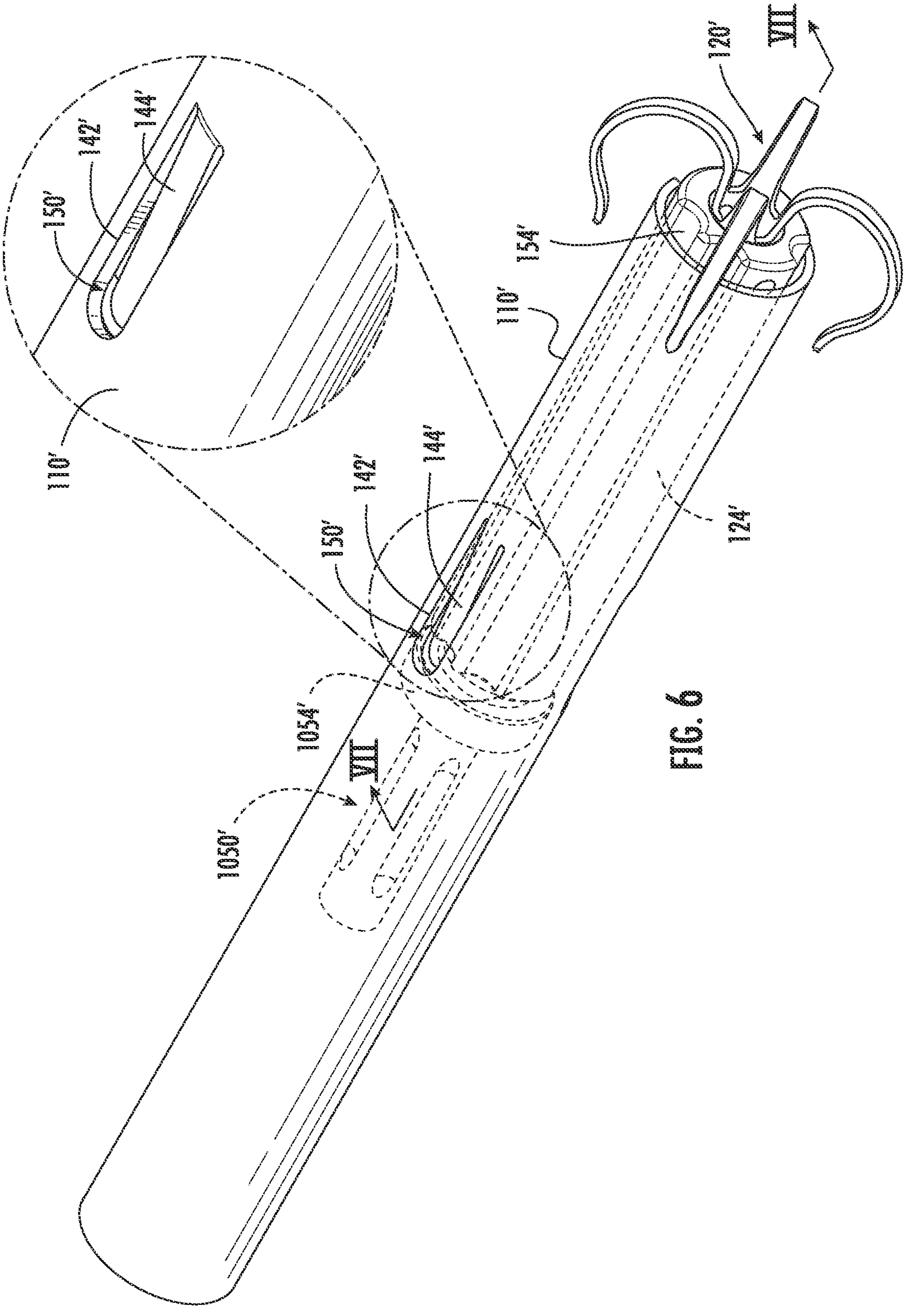
FIG. 6 illustrates a perspective view of another example of an embodiment of an anchor delivery and deployment device and system formed in accordance with various principles of the present disclosure, with an anchor illustrated in phantom.
Figure 7:
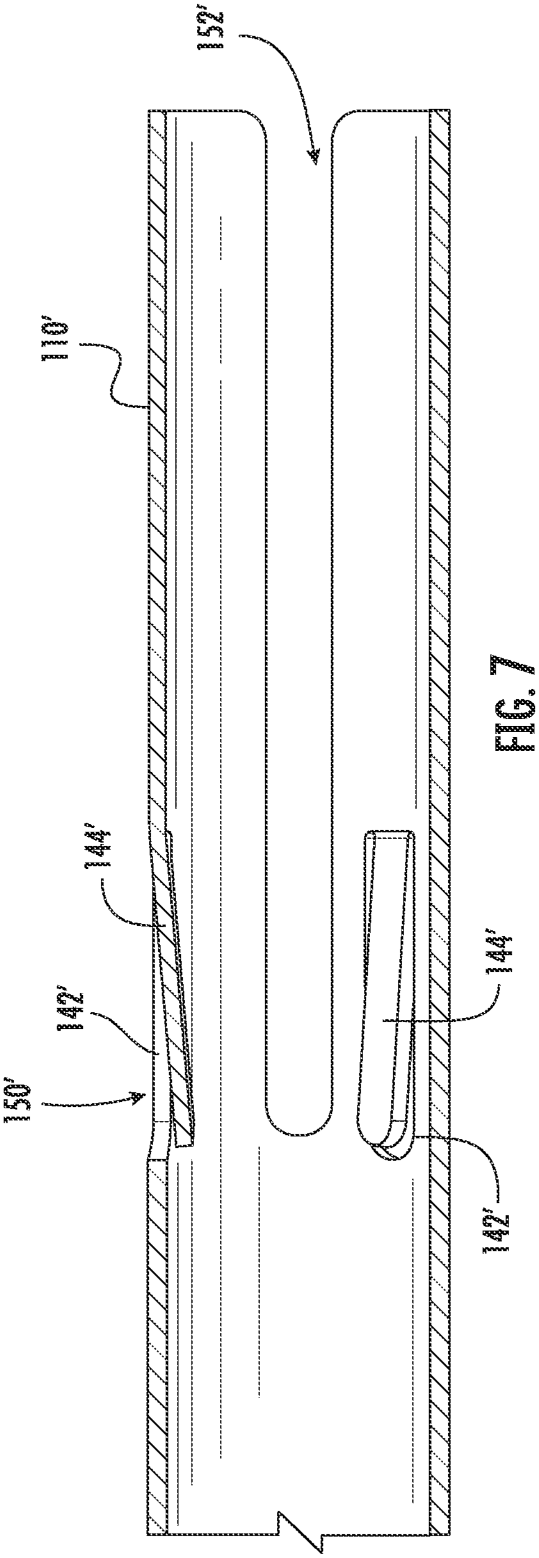
FIG. 7 illustrates a cross-sectional view along line VII-VII of FIG. 6.

In accordance with various principles of the present disclosure, a longitudinal groove may be provided along the exterior surface of the anchor housing 124 of the embodiment of an implantable device delivery/deployment system 100 such as illustrated in FIGS. 4A-4D, FIG. 5A, and FIG. 5B to assure that the radially-inwardly-directed tab 144 does not interfere with axial movement of the anchor housing 124 (such as to deploy the anchor 120). In the example of an alternate embodiment of an implantable device delivery/deployment system 100' illustrated in FIG. 6, the anchor housing 124' has one or more circumferentially spaced apart longitudinal grooves 154' along the exterior thereof. Such grooves may be spaced equidistantly or otherwise, such as in consideration of configurations of other associated devices or structures. In some embodiments, the longitudinal grooves 154' are scalloped or scooped along at least a portion of the longitudinal extent of the anchor housing 124'. Such longitudinal grooves 154' ensure that a radially-inwardly directed tab 144' in the anchor garage 110' does not rub or interfere with axial movement of the anchor 120' as the anchor 120' is advanced or retracted in a manner as described above with respect to the example of an embodiment illustrated in FIGS. 4A-4D. Additionally or alternatively, the longitudinal grooves 154' may cooperate with the tab 144' formed on the anchor garage 110' to together form an implantable-device-rotation-limiter arrangement 150'. Like the implantable-device-rotation-limiter arrangement 150 illustrated in FIGS. 4A-4D and FIG. 5, the implantable-device-rotation-limiter arrangement 150' illustrated in FIG. 6 inhibits/prevents rotational movement of the anchor housing 124' with respect to the anchor garage 110', such as upon rotation of the stylet 1050' to actuate an artificial chordae tendineae tensioning and locking device 130' operatively associated with the anchor 120' and/or to withdraw/dissociate from the anchor 120'. The artificial chordae tendineae tensioning and locking device 130' may be configured as the artificial chordae tendineae tensioning and locking device 130 illustrated in FIG. 5A and FIG. 5B, or otherwise. In some embodiments, the anchor garage 110' includes more than one tab 144', each tab 144' fitting within a different longitudinal groove 154' along the anchor housing 124'. Such tab 144' are illustrated in further detail in FIG. 7, illustrating a cross-sectional view of FIG. 6 along line VII-VII.

Various modifications and substitutions may be made to the above-described examples of implantable-device-extension-limiter arrangements and/or implantable-device-rotation-limiter arrangements. For instance, the shape, number, configuration, etc., of the stopper component of the implantable-device-extension-limiter arrangement may be varied. For instance, more than one stopper component (e.g., tab) may be provided along the circumference of the anchor garage, such as to distribute stopping forces with respect to the corresponding stopper component associated with the stylet, such as in the example of an embodiment illustrated in FIG. 6 and FIG. 7. Moreover, although the cut 142 forming the stopper 144 of the implantable-device-extension-limiter component in the anchor garage 110 illustrated in FIG. 3A is generally rectangular, other shapes of cuts and/or stoppers are within the scope and spirit of the present disclosure. For instance, the cut 142' forming the tab 144' of the implantable-device-extension-limiter component in the anchor garage 110' illustrated in FIG. 6 and FIG. 7 is curved rather than rectangular, as illustrated in the detail view of FIG. 6.

It will be appreciated that extension limiter arrangements as described herein can be utilized for any deployable/implantable device that requires a prescribed deployment depth, and are not limited to anchors as described herein. Moreover, it will be appreciated that rotation limiter arrangements as described herein can be utilized for any implantable device delivery/deployment system to which rotational motion may be imparted (e.g., from a handle or other delivery/deployment device or component) but which may need rotation of the implantable device to be limited.

Although reference is made generally to a delivery/deployment system, it will be appreciated that such system may provide and/or perform other actions, and may include further delivery/deployment systems and devices for various components of the overall system.

It is to be understood by one of ordinary skill in the art that the present discussion is a description of illustrative examples of embodiments only, and is not intended as limiting the broader aspects of the present disclosure. All apparatuses and methods discussed herein are examples of apparatuses and/or methods implemented in accordance with one or more principles of this disclosure. These examples are not the only way to implement these principles but are merely examples, not intended as limiting the broader aspects of the present disclosure. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. It will be appreciated features described with respect to one embodiment typically may be applied to another embodiment, whether or not explicitly indicated. The various features hereinafter described may be used singly or in any combination thereof. Therefore, the present invention is not limited to only the embodiments specifically described herein.

Thus, although embodiments of the present disclosure may be described with specific reference to an implant for use with mitral valves, it is appreciated that various other implants may similarly benefit from the structures and manufacturing methods disclosed herein. For example, implants which must withstand the palpatory forces for repairing a tricuspid valve annulus and/or addressing other dilatation, valve incompetency, valve leakage, and other similar heart failure conditions may also benefit from the concepts disclosed herein.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. As used in this specification and the appended claims, the term "or" is generally employed in its sense including "and/or" unless the content clearly dictates otherwise. As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, engaged, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the terms "comprises", "comprising", "includes", and "including" do not exclude the presence of other elements, components, features, groups, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A delivery/deployment system for delivering and/or deploying a tissue anchor with respect to a treatment site, said delivery/deployment system comprising:
- a leaflet clip spreader;
- a leaflet clip operatively associated with said leaflet clip spreader;
- an anchor garage;
- an anchor operatively associated with said anchor garage;
- a stylet operatively coupled with said anchor to move said anchor distally with respect to said anchor garage;
- an implantable-device-extension-limiter arrangement comprising an anchor garage stopper component extending inwardly from a wall of said anchor garage, and a stylet stopper component operatively associated with said stylet;
- wherein said stylet stopper component is configured to engage with said anchor garage stopper component to limit the distance said stylet may extend said anchor distally out of said anchor garage;
- wherein said anchor garage has a wall defining a lumen therein, and said anchor is positionable within the anchor garage lumen;
- wherein said anchor garage stopper component comprises a tab formed by a cut in said anchor garage wall and bent radially-inwardly into the lumen defined within said anchor garage; and
- wherein said anchor comprises an anchor housing with a longitudinal groove into which said tab in said anchor garage wall extends to limit rotational movement of said anchor with respect to said anchor garage.

2. The delivery/deployment system of claim 1, wherein said stylet stopper component comprises a radially-expanded portion engageable with said tab in said anchor garage wall to limit distal extension thereof relative to said anchor garage.

3. A delivery/deployment system for delivering and/or deploying a tissue anchor with respect to a treatment site, said delivery/deployment system comprising:
- a leaflet clip spreader;
- a leaflet clip operatively associated with said leaflet clip spreader;
- an anchor garage;
- an anchor operatively associated with said anchor garage;
- a stylet operatively coupled with said anchor to move said anchor distally with respect to said anchor garage;
- an implantable-device-extension-limiter arrangement comprising an anchor garage stopper component extending inwardly from a wall of said anchor garage, and a stylet stopper component operatively associated with said stylet;
- wherein said stylet stopper component is configured to engage with said anchor garage stopper component to limit the distance said stylet may extend said anchor distally out of said anchor garage;
- wherein:
- said stylet is rotatably dissociable from said anchor; and
- said anchor comprises a rotation-limiter component operatively engaged with an anchor garage rotation-limiter component to inhibit rotation of said anchor as said stylet is rotated.

4. The delivery/deployment system of claim 3, wherein:
- said anchor garage has a wall defining a lumen therein;
- said anchor garage rotation-limiter component comprises a longitudinally extending slot in said anchor garage wall;

said anchor is positioned within the anchor garage lumen; and said anchor rotation-limiter component comprises a radially-outwardly extending projection extending into said slot in said anchor garage wall.

5. The delivery/deployment system of claim 3, wherein:

said anchor garage has a wall defining a lumen therein;

said anchor is positioned within the anchor garage lumen;

said anchor garage stopper component comprises a radially-inwardly extending component projecting into the anchor garage lumen;

said anchor comprises an anchor housing operatively associated therewith;

said anchor rotation-limiter component comprises a longitudinally-extending groove extending along said anchor housing; and said anchor garage stopper component extends into the longitudinally-extending groove along said anchor housing to comprise said anchor garage rotation-limiter component.

6. The delivery/deployment system of claim 5, wherein said anchor garage stopper comprises a tab formed by a cut in said anchor garage wall and bent radially-inwardly into the lumen defined within said anchor garage and extending into the longitudinally-extending groove along said anchor housing.

7. A delivery/deployment system for delivering and/or deploying a tissue anchor with respect to a treatment site, said delivery/deployment system comprising:

a leaflet clip spreader;

a leaflet clip operatively associated with said leaflet clip spreader;

an anchor garage;

an anchor operatively associated with said anchor garage;

a stylet operatively coupled with said anchor to move said anchor distally with respect to said anchor garage;

an implantable-device-extension-limiter arrangement comprising an anchor garage stopper component extending inwardly from a wall of said anchor garage, and a stylet stopper component operatively associated with said stylet;

wherein said stylet stopper component is configured to engage with said anchor garage stopper component to limit the distance said stylet may extend said anchor distally out of said anchor garage;

wherein:

said anchor further comprises a housing;

an artificial chordae tendineae tensioning and locking device is operatively associated with said anchor housing;

said system further comprises an artificial chordae tendineae coupled between said leaflet clip and said artificial chordae tendineae tensioning and locking device;

said stylet is operatively coupled with said artificial chordae tendineae tensioning and locking device to actuate said artificial chordae tendineae tensioning and locking device; and said anchor comprises a rotation-limiter component operatively engaged with an anchor garage rotation-limiter component to inhibit rotation of said anchor as said stylet is rotated to actuate said artificial chordae tendineae tensioning and locking device.

8. The delivery/deployment system of claim 7, wherein:

said anchor garage has a wall defining a lumen therein;

said anchor garage rotation-limiter component comprises a longitudinally extending slot in said anchor garage wall;

said anchor is positioned within the anchor garage lumen;

said anchor rotation-limiter component comprises a radially-outwardly extending projection extending into said slot in said anchor garage wall; and said artificial chordae tendineae extends from said leaflet clip to said anchor through the slot in said anchor garage wall.

* * * * *